United States Patent [19]
Hausheer et al.

[11] Patent Number: 6,037,336
[45] Date of Patent: Mar. 14, 2000

[54] REDUCING TOXIC EFFECTS OF CARBOPLATIN USING DITHIOETHERS

[75] Inventors: Frederick H. Hausheer, Boerne; Kochat Haridas, San Antonio; Dhanabalan Murali, San Antonio; Seetharamulu Peddaiahgari, San Antonio; Dasharatha G. Reddy, San Antonio, all of Tex.

[73] Assignee: BioNumerik Pharmaceuticals, Inc., San Antonio, Tex.

[21] Appl. No.: 09/269,360

[22] PCT Filed: Sep. 23, 1997

[86] PCT No.: PCT/GB97/02582

§ 371 Date: May 10, 1999

§ 102(e) Date: May 10, 1999

[87] PCT Pub. No.: WO98/11898

PCT Pub. Date: Mar. 26, 1998

Related U.S. Application Data

[60] Provisional application No. 60/026,430, Sep. 23, 1996.

[30] Foreign Application Priority Data

Jul. 30, 1998 [JP] Japan ................................. 10-215512

[51] Int. Cl.[7] ........................... A61K 31/66; A61K 31/28; A61K 31/185

[52] U.S. Cl. ........................... 514/102; 514/126; 514/492; 514/553

[58] Field of Search ..................................... 514/492, 102, 514/126, 553

[56] References Cited

U.S. PATENT DOCUMENTS 5,789,000  8/1998  Hausheer et al. ....................... 424/649

*Primary Examiner*—Jerome D. Goldberg
*Attorney, Agent, or Firm*—Thomas J. Dodd

[57] ABSTRACT

To reduce the toxic effect of carboplatin, particularly myelo-suppression and emesis, a dithioether having the formula $R_1\text{-}(CH_2)_n\text{—}S\text{—}S\text{—}(CH_2)_m\text{—}R_2$ (I) wherein:

each of $R_1$ and $R_2$ individually is $SO_3H$ or $PO_3H_2$; and
each of m and n is individually 1, 2, 3 or 4;

or a pharmaceutically acceptable salt thereof, preferably disodium 2,2'-dithiobis(ethane sulfonate) (dimesna), is administered in combination with carboplatin to a patient, at substantially the same time or sequentially, whereby the dithioether and the carboplatin become co-present in the blood of the patient. Compositions comprising carboplatin and the dithioether are included in the invention.

11 Claims, No Drawings

REDUCING TOXIC EFFECTS OF CARBOPLATIN USING DITHIOETHERS

This application claims benefit of Provisional Application 60/026,430 filed Aug. 23, 1996.

FIELD OF THE INVENTION

This invention relates to reducing the toxicity of carboplatin (cis-diammine-1,1-cyclobutanedicarboxylato-platinum II, CBDCA, JM-8 and NSC 241240), using a dithioether as a protective agent.

BACKGROUND OF THE INVENTION

Carboplatin (hereinafter also referred to as "CBDCA" or "CBP") is a widely used anticancer drug which is normally used in combination with other anticancer drugs in the treatment of cancers of the lung, head and neck, ovary, esophagus, bladder, testis, and others. One of the most important and common dose limiting toxicities of carboplatin is hematological toxicity. In particular, myelosuppression (depression of blood elements formed within bone marrow) is often manifested in the form of thrombocytopenia, neutropenia, leukopenia, and various forms of anemia. The other major carboplatin-induced toxicity is gastro-intestinal (causing nausea and vomiting).

In order for carboplatin to react with certain nucleic acid sequences in cellular DNA, it must first undergo chemical conversion to an active species by the partial or complete displacement of the cyclobutanedicarboxylato (CBDC) ligands, respectively, by chloride. The chloro and dichloro species are believed to act against cancer cells by reacting with the imidazole nitrogens on DNA. These chloro species are believed to be metabolised in vivo to active hydroxy species.

Carboplatin, unlike cisplatin, is relatively stable in the body. Its cyclobutanedicarboxylato (CBDC) group makes it much less susceptible to displacement by incoming nucleophiles. It is less active than cisplatin towards DNA. Indeed, it is generally given in combination with other anti-cancer drugs. Although less prone to cause the nephrotoxicity associated with cisplatin, it is highly myelotoxic and has gastrointestinal toxicity. It might at first be thought that carboplatin, with its active chloro species, should behave similarly to cisplatin and therefore be further metabolised in the same way. However, this is not so: the body cells most adversely affected by carboplatin-induced toxicity (bone marrow and GI tract cells) are different from those most adversely affected by cisplatin (kidney cells). Thus, the metabolic species responsible for the toxicity cannot be the same. Finding a protective agent for carboplatin therefore represents a new and separate problem from that presented by cisplatin.

SUMMARY OF THE INVENTION

It has now been found that a dithioether having the formula $R_1—(CH_2)_n—S—S—(CH_2)_m—R_2$ (I) wherein:

each of $R_1$ and $R_2$ individually is $SO_3H$ or $PO_3H_2$; and
each of m and n is individually 1, 2, 3 or 4; or a pharmaceutically acceptable salt thereof, is a suitable protective agent for carboplatin.

This invention can be represented in different ways according to local patent law. Thus, it includes the use of the dithioether in the manufacture of a medicament for administration in combination with carboplatin to a patient, at substantially the same time or sequentially, whereby the dithioether and the carboplatin become co-present in the blood of the patient and the dithioether serves to reduce the toxicity of the carboplatin. It further includes a method of treating a patient suffering from a cancer susceptible to carboplatin therapy, which comprises administering the dithioether to the patient at the above-recited time. Also within the invention is a medicament for treating cancer in combination with carboplatin therapy, comprising the dithioether.

The preferred dithioether is sodium 2,2'-dithiobis (ethanesulfonate), herein abbreviated to dimesna.

The invention is useful in relation to any cancer treatable by a therapy consisting of or including administration of carboplatin, especially the cancers specifically listed above.

The invention also includes a composition suitable for administration to patients with cancer, comprising carboplatin and a dithioether as defined above, especially in the form of a sterile injectable solution, preferably of pH 2 to 6.

DESCRIPTION OF THE PREFERRED EMBODIMENTS

The carboplatin formulation used in the invention will typically be a solution. It can take any form appropriate to or conventional for formulation of carboplatin. The type of formulation will of course depend on the route of administration, which will normally be parenteral, especially intravenous, and preferably by injection. The preferred solvent is aqueous, since carboplatin has a water-solubility of 14 mg/mL. The formulation will normally contain from 0.05 mg/mL up to the maximum solubility of carboplatin. It may also include mannitol (a preservative). It may contain other excipient(s) and/or diluent(s).

The carboplatin formulation will normally have a pH of from 2 to 6; a neutral pH of about 7 is much less preferred. Any pharmaceutically acceptable acid, including hydrochloric acid, may be used to adjust the pH. However, a formulation which is substantially free of added chloride ions, or, at least, free of chloride ions from added sodium chloride, has been shown to have improved stability. Cisplatin, by contrast, is preferably formulated in a chloride ion solution, such as isotonic or hypertonic saline for injection.

The dithioether protective agent is formulated separately from the carboplatin. For oral administration, it may be formulated as a tablet, capsule, caplet, colloidal suspension or solution, or other form which is easily ingested by the patient. For parenteral administration it is preferably formulated as a sterile injectable solution, as described above. The oral and/or parenteral formulation may be stored as an aqueous solution or as a lyophilized powder suitable for reconstitution with water or another solvent.

Hereinafter, the dithioether will be discussed mainly with reference to disodium 2,2'-dithiobis(ethanesulfonate) (dimesna), but the person skilled in the art will readily be able to use the principles of this invention in relation to other dithioethers of formula (I), especially a compound of formula (I) in which m and n are from 1 to 3, in the form of a sodium salt.

The preferred dithioethers are the sulfonates, especially the disodium salts thereof, but including the monosodium, monopotassium, sodium-potassium, dipotassium, calcium and magnesium salts of the sulfonate. Further, since it is the dithio group which must provide a reactive nucleophile for quenching the reactive species of carboplatin and the sulfonate group confers water-solubility on the molecule, it follows that the sulfonate group could be replaced by phosphonate. Thus, disodium and tetrasodium 2,2'-dithiobis (ethanephosphonates) are also preferred dithioethers for use in the invention.

For the dithioether formulation, the preferred solvent is aqueous, since the dithioethers are also water-soluble, e.g. up to 300 mg/mL for dimesna. The concentration of dithioether is normally from 1 mg/mL up to the maximum solubility. In principle, higher amounts of the dithioether are usable, e.g. up to 500 mg/mL, although, of course, solubility problems may arise. The formulation may contain excipient(s) and/or diluent(s).

The carboplatin/dithioether combination can be administered to human or non-human patients as a treatment for various types of cancer, as described in the effectiveness profile for carboplatin. It may be administered as a "single drug therapy" (carboplatin being the sole cytotoxic or anticancer therapeutic agent) or in combination with other cytotoxic, anti-cancer or other chemotherapeutic agents.

Typically, the carboplatin and the dithioether formulations will be prepared as for intravenous injection in sterile, single-dose containers. Both could be administered orally.

Preferably the dithioether is administered before the carboplatin, especially from 5 minutes to 1 hour before. For dimesna, from 15 to 30 minutes before has been found very effective. Administration of the combination of carboplatin and the dithioether may require adjustments in one or both of timing and/or dosage. The goal in the treatment is to match the peak in vivo concentration of the dithioether with that of the toxic metabolites of carboplatin. Although carboplatin reacts slowly in vivo to produce the active nucleophilic species which ultimately cause damage in certain cells, especially bone marrow and GI tract cells, it has been found that at least the greater proportion of the dose of dithioether should be given before the carboplatin, although it will sometimes be helpful to give the remaining, smaller proportion, of the dose of dithioether after the carboplatin, in order to combat the effects of slowly-generated or long-lasting active nucleophilic species of carboplatin. Carboplatin has a relatively long half-life in the body. Desirability and necessity of additional doses of protective agent is determined by carefully monitoring the patient's excretion of platinum to estimate the rate of drug elimination from the body.

The invention includes the possibility of administering at least a part of the dithioether in the form of a composition comprising the carboplatin and the dithioether components, preferably as an aqueous solution of pH 2 to 6. Features of preference of such compositions are as recited above for the individual components.

The carboplatin can be administered in any conventional dose. It may be possible to exceed the conventional dose of carboplatin, as this is frequently limited by the toxicity problem which the present invention mitigates. The carboplatin dose will normally be in the range 0.3 to 45 mg/kg (a corresponding dose of dithioether would then be from 20 to 2500 mg/kg, increasing roughly proportionately with the carboplatin dose). In terms of body surface area, ranges of 100 to 1000 mg/m$^2$ of carboplatin and 1000 to 40,000 mg/m$^2$ of dithioether are suggested.

Since the toxicity of the protective agent is very low (the parenteral and oral $LD_{50}$ values for all of the dithioethers of formula I are generally higher than that of common table salt, and all are rapidly eliminated through excretion in the urine), large amounts of the protective agent may be given either orally or parenterally to provide constant and safe protection against any residual carboplatin toxicity. Thus, typically the weight ratio of carboplatin to dithioether used in the therapy is from 6:1 to 1000:1, most especially 25:1 to 700:1.

The following non-limiting Examples illustrate the invention. The vials referred to are "amber vials", which protect the carboplatin from exposure to light. Although Examples 1 to 4 relate to solutions of carboplatin and the dithioether together, it will be appreciated that they can be formulated separately, with the carboplatin at acidic pH and each active component at the concentration indicated in the solutions of the Examples.

EXAMPLE 1

(a) Preparation of 2,2'-dithiobis(ethanesulfonate) (dimesna)

Disodium 2,2'-dithiobis(ethanesulfonate) was prepared by oxidizing 2-mercaptoethanesulfonate in water with an equimolar amount of iodine as previously reported by L. Lamaire and M. Reiger, J. Org. Chem. 26, 1330–1, (1961). The other sulfonate and phosphonate dithioethers of formula (I) can be prepared analogously.

(b) Stability of dimesna 50 mg of the dimesna thus prepared were dissolved in 1 mL of water and the pH of the solution adjusted to 1.5, 2.0, 3.0, 4.0, 5.0 and 6.0 by adding in hydrochloric acid in water or the pH adjusted to 8.0 and 9.0 by adding 1 N sodium hydroxide in water. The solution was then stirred for 24 hours at room temperature, the water was removed at reduced pressure and the residue dissolved in spectral grade $D_2O$. The proton NMR spectrum gave only peaks corresponding to the starting material. Heating the pH 1.5 solution to 100° C. for 10 minutes gave no change in the proton NMR spectrum. These data indicate that dimesna is stable in aqueous solution at pH 1.5 to 9.0.

(c) Preparation of a sterile solution of carboplatin and dimesna

Pure hydrochloric acid (99.999%) was added to a sterile, injectable, Lactated Ringer's (LR) solution (US Pharmacopoeia grade), to give a pH in the range 2.0 to 6.0. 1 mg of pure carboplatin/mL of the above LR solution was added and allowed to completely dissolve by agitation (1500–2500 rpm) at room temperature, for approximately 60 to 90 minutes in the dark. Then, 15 mg of dimesna, prepared above, per mL of solution were added and the mixture agitated until complete dissolution occurred. The final pH was adjusted to within the range pH 2.0 to 6.0 by adding further pure hydrochloric acid. The solution was sterilized by filtration through a sterile 0.2 micrometre filter (obtained from VWR Scientific) and stored in sterile injection vials. Each vial contained approximately 0.9 mg of carboplatin and 14.3 mg of dimesna per mL of solution.

EXAMPLE 2

To a sterile injectable aqueous solution of LR solution (USP grade) were added 15 mg of dimesna/mL of solution. The dimesna was allowed to dissolve completely by agitation (1500–2500 rpm) at room temperature, for 5–10 minutes. The pH of the solution was adjusted to within the range 2.0 to 6.0 by adding pure (99.999%) hydrochloric acid. 1 mg/mL of dimesna solution of pure (98.0%) carboplatin was added and the mixture agitated in the dark until complete dissolution occurred. The remaining steps were as in Example 1 (c), giving a solution of the same approximate composition. Each vial contained approximately 1.0 mg of carboplatin and 14.3 mg of dimesna per mL of injection solution.

EXAMPLE 3

Example 1(c) was repeated except that 0.5 mg/mL of carboplatin and 30 mg/mL of dimesna were used. Each vial contained 0.5 mg of carboplatin and 12.9 mg of dimesna per mL of injection solution.

EXAMPLE 4

Example 1(c) was repeated except that pure mannitol (99+% purity, from Aldrich Chemical Company) was dissolved in the LR solution, to give a concentration of 1.0% w/v mannitol, and also that 30 mg/mL of dimesna were used. Each vial contained approximately 1.0 mg of carboplatin and 12.9 mg of dimesna per mL of injection solution.

EXAMPLE 5

Use of Dimesna to Reduce Carboplatin Toxicity

Experiments were performed to determine the efficacy of dimesna in reducing the toxicity of carboplatin in adult beagle dogs. Toxic effects were tested at varying dose levels of carboplatin, with or without administration of dimesna. The carboplatin used was an aqueous solution from vials of "Paraplatin" (Bristol Myers Squibb) and injected i.v. by a slow drip over 5 to 10 minutes. Lyophilised dimesna was reconstituted in water and injected i.v. 30 minutes before the carboplatin.

Table 1 gives the dosing schedule followed in the experiments, with two animals, one male and one female in each group.

TABLE 1

| Group | Dimesna (mg/kg) | Carboplatin (mg/kg) |
|---|---|---|
| 1 | 0 | 45 |
| 2 | 2000 | 45 |
| 3 | 0 | 30 |
| 4 | 2000 | 30 |
| 5 | 0 | 20 |
| 6 | 2000 | 20 |
| 7 | 0 | 13 |
| 8 | 2000 | 13 |
| 9 | 2000 | 0 |

The animals were closely observed after the dose was administered, and euthanized on day 30 for tissue necropsy. Tissues were trimmed, processed, and stained slides were prepared of the following: thymus, heart, lung, stomach, duodenum, jejunum, colon, pancreas, liver, kidney, urinary bladder, testis, ovary, spleen, mesenteric and mandibular lymph nodes, bone marrow, ischiatic nerve, and all gross lesions. Lesions found were graded from one to five based upon severity.

Results

Three dogs, the two from control Group 1 which received only a 45 mg/kg dose of carboplatin, and the female from control Group 3 (30 mg/kg carboplatin only), died or were sacrificed because of their moribund condition prior to day 30. Most of the other dogs from control Groups 3, 5 and 7 exhibited moderate to severe cellular depletion of femoral bone marrow, moderate to severe lymphoid depletion of the thymus, and other microscopic lesions, particularly in the gastrointestinal tract. The dogs from the Groups 2, 4, 6 and 8, which were given dismesna, all survived for the duration of the experiment. Dogs from Groups 4, 6 and 8 showed no cellular depletion of the femoral bone marrow or lymphoid depletion in the thymus. The dogs from Group 2, which received in essence, a lethal dose of carboplatin, both survived and exhibited only mild lymphoid depletion, with no evident cellular depletion of bone marrow. Group 9 control dogs which received only dimesna showed no physiological changes.

What is claimed is:

1. A method for reducing the unwanted toxicity of carboplatin, said method comprising administering to a patient an effective amount of a dithioether having the formula $R_1-(CH_2)_n-S-S-(CH_2)_m-R_2$ (I) wherein:

each of $R_1$ and $R_2$ individually is $SO_3H$ or $PO_3H_2$; and each of m and n is individually 1, 2, 3 or 4; or a pharmaceutically acceptable salt thereof and an effective amount of carboplatin, at substantially the same time or in a sequential manner.

2. The method of use according to claim 1, wherein the dithioether is administered to the patient prior to the administration of carboplatin.

3. The method of use according to claim 2, wherein the dithioether is administered at a time from 5 minutes prior to 1 hour prior to the administration of carboplatin.

4. The method of use according to claim 1, 2 or 3, wherein the dithioether and the carboplatin are administered either both intravenously or both orally.

5. The method of use according to claim 1, 2, 3 or 4, wherein the weight ratio of dithioether to carboplatin administered is from 25:1 to 700:1.

6. The method of use according to claim 1, 2, 3, 4 or 5, wherein the dithioether is a compound of formula (I) in which m and n are from 1 to 3, in the form of a sodium salt.

7. The method of use according to claim 6, wherein the dithioether is dimesna, being the compound of formula (I) in which m and n are 2 and $R_1$ and $R_2$ are $SO_3H$, in the form of the disodium salt.

8. The method of use according to claim 7, wherein the dimesna is administered from 15 to 30 minutes before the carboplatin.

9. A composition suitable for administration to patients with cancer, comprising an effective amount of carboplatin and a dithioether having the formal R1—(CH2)n—S—S—(CH2)m—R2 (I) wherein: each of R1 and R2 individually is SO3H or PO3H2; and each of m and n is individually 1, 2, 3 or 4; or a pharmaceutically acceptable salt thereof.

10. A composition according to claim 9, in the form of a sterile injectable aqueous solution or suspension of pH 2 to 6.

11. A composition according to claim 10, wherein the weight ratio of dithioether to carboplatin is from 25:1 to 700:1.

* * * * *